(12) United States Patent
Aklivanh et al.

(10) Patent No.: US 11,896,327 B1
(45) Date of Patent: Feb. 13, 2024

(54) TISSUE SENSING CIRCUIT FOR SURGICAL INSTRUMENT

(71) Applicant: Cilag GmbH International, Zug (CH)

(72) Inventors: Eyal Aklivanh, Belmont, CA (US); Sean C. Eves Knudsen, Oakland, CA (US); Darshini Balamurugan, San Jose, CA (US); Lewis T. Cronis, Mendon, MA (US); Zhijun Liu, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/089,723

(22) Filed: Dec. 28, 2022

(51) Int. Cl.
| | | |
|---|---|---|
| *A61B 17/072* | (2006.01) | |
| *A61B 34/30* | (2016.01) | |
| *A61B 17/00* | (2006.01) | |
| *A61B 17/068* | (2006.01) | |
| *A61B 34/00* | (2016.01) | |
| *A61B 17/115* | (2006.01) | |

(52) U.S. Cl.
CPC ............ *A61B 34/30* (2016.02); *A61B 17/072* (2013.01); *A61B 17/068* (2013.01); *A61B 17/115* (2013.01); *A61B 34/71* (2016.02); *A61B 2017/00026* (2013.01); *A61B 2017/00398* (2013.01); *A61B 2017/07214* (2013.01)

(58) Field of Classification Search
CPC ............... A61B 17/068; A61B 17/072; A61B 17/07207; A61B 17/115; A61B 2017/00026; A61B 2017/07214; A61B 2017/07271; A61B 2017/00221; A61B 2017/2927; A61B 34/30; A61B 34/71

USPC .............. 227/19, 175.1, 175.2, 176.1, 180.1; 606/1, 139, 219

See application file for complete search history.

(56) References Cited

U.S. PATENT DOCUMENTS

| | | | |
|---|---|---|---|
| 5,624,452 A | * | 4/1997 | Yates ................. A61B 18/1447 606/139 |
| 6,500,176 B1 | | 12/2002 | Truckai et al. |
| 6,775,575 B2 | | 8/2004 | Bommannan et al. |
| 6,783,524 B2 | | 8/2004 | Anderson et al. |
| 7,380,696 B2 | | 6/2008 | Shelton, IV et al. |
| 7,695,485 B2 | | 4/2010 | Whitman et al. |

(Continued)

OTHER PUBLICATIONS

Analog Devices, Impedance Measurement & Analysis, dated May 29, 2022, downloaded from https://www.analog.com/en/applications/markets/instrumentation-and-measurement-pavilion-home/electronic-test-and-measurement/impedance-measurement-and-analysis.html, 21 pgs.

*Primary Examiner* — Scott A Smith
(74) *Attorney, Agent, or Firm* — Frost Brown Todd LLP

(57) ABSTRACT

A surgical instrument includes an end effector having first and second jaws that cooperate to clamp in vivo material of a patient, and a first electrode that delivers an electrical signal to the in vivo material. The instrument further includes a second electrode that receives the electrical signal from the first electrode, and an electrical circuit housed within the end effector. The electrical circuit includes a microcontroller that controls delivery of the electrical signal to the first electrode, where the electrical signal passes through the in vivo material to the second electrode. The electrical circuit also determines an electrical impedance of the in vivo material and determines at least one of a presence or absence of tissue in the in vivo material, or a characteristic of tissue in the in vivo material.

20 Claims, 19 Drawing Sheets

(56) References Cited

U.S. PATENT DOCUMENTS

| | | | |
|---|---|---|---|
| 8,118,206 B2 * | 2/2012 | Zand | A61B 5/0086 |
| | | | 227/176.1 |
| 8,157,145 B2 * | 4/2012 | Shelton, IV | A61B 17/07207 |
| | | | 227/19 |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,888,809 B2 | 11/2014 | Davison et al. | |
| 8,939,974 B2 | 1/2015 | Boudreaux et al. | |
| 9,161,803 B2 | 10/2015 | Yates et al. | |
| 9,186,142 B2 | 11/2015 | Fanelli et al. | |
| 9,517,065 B2 | 12/2016 | Simms et al. | |
| 9,526,565 B2 | 12/2016 | Strobl | |
| 9,545,253 B2 | 1/2017 | Worrell et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,877,720 B2 | 1/2018 | Worrell et al. | |
| 10,092,292 B2 | 10/2018 | Boudreaux et al. | |
| 10,828,028 B2 * | 11/2020 | Harris | G16H 20/40 |
| 11,241,269 B2 | 2/2022 | Brady et al. | |
| 11,642,125 B2 * | 5/2023 | Harris | A61B 17/320068 |
| | | | 227/180.1 |
| 2003/0093103 A1 | 5/2003 | Malachowski et al. | |
| 2005/0131390 A1 | 6/2005 | Heinrich et al. | |
| 2006/0273135 A1 * | 12/2006 | Beetel | A61B 17/128 |
| | | | 227/175.1 |
| 2008/0251568 A1 * | 10/2008 | Zemlok | A61B 17/072 |
| | | | 606/41 |
| 2008/0296346 A1 * | 12/2008 | Shelton, IV | A61B 34/71 |
| | | | 227/180.1 |
| 2011/0036887 A1 * | 2/2011 | Zemlok | A61B 17/07207 |
| | | | 227/175.1 |
| 2012/0012636 A1 * | 1/2012 | Beckman | A61B 17/07207 |
| | | | 227/175.1 |
| 2012/0193396 A1 * | 8/2012 | Zemlok | A61B 17/07207 |
| | | | 227/176.1 |
| 2016/0066916 A1 * | 3/2016 | Overmyer | H02H 3/207 |
| | | | 227/176.1 |
| 2016/0166256 A1 * | 6/2016 | Baxter, III | A61B 17/07207 |
| | | | 227/176.1 |
| 2021/0059672 A1 | 3/2021 | Giordano et al. | |

\* cited by examiner

TISSUE SENSING CIRCUIT FOR SURGICAL INSTRUMENT

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely illustrative surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; and U.S. Pat. No. 11,241,269, entitled "Surgical Devices Switchable Between Monopolar Functionality and Bipolar Functionality," issued Feb. 8, 2022. The disclosure of each of the above-cited U.S. Patents and U.S. Patent Publications is incorporated by reference herein.

Other endoscopic surgical instruments may include a tissue cutting element and one or more elements that transmit energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein, in its entirety; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein, in its entirety; U.S. Pat. No. 8,888,809, entitled "Surgical Instrument with Jaw Member," issued Nov. 18, 2014, the disclosure of which is incorporated by reference herein, in its entirety; U.S. Pat. No. 9,161,803, entitled "Motor Driven Electrosurgical Device with Mechanical and Electrical Feedback," issued Oct. 20, 2015, the disclosure of which is incorporated by reference herein, in its entirety; U.S. Pat. No. 9,877,720, entitled "Control Features for Articulating Surgical Device," issued Jan. 30, 2018, the disclosure of which is incorporated by reference herein, in its entirety; U.S. Pat. No. 9,545,253, entitled "Surgical Instrument with Contained Dual Helix Actuator Assembly," issued Jan. 17, 2017, the disclosure of which is incorporated by reference herein, in its entirety; and U.S. Pat. No. 9,526,565, entitled "Electrosurgical Devices," issued Dec. 27, 2016, the disclosure of which is incorporated by reference herein, in its entirety.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
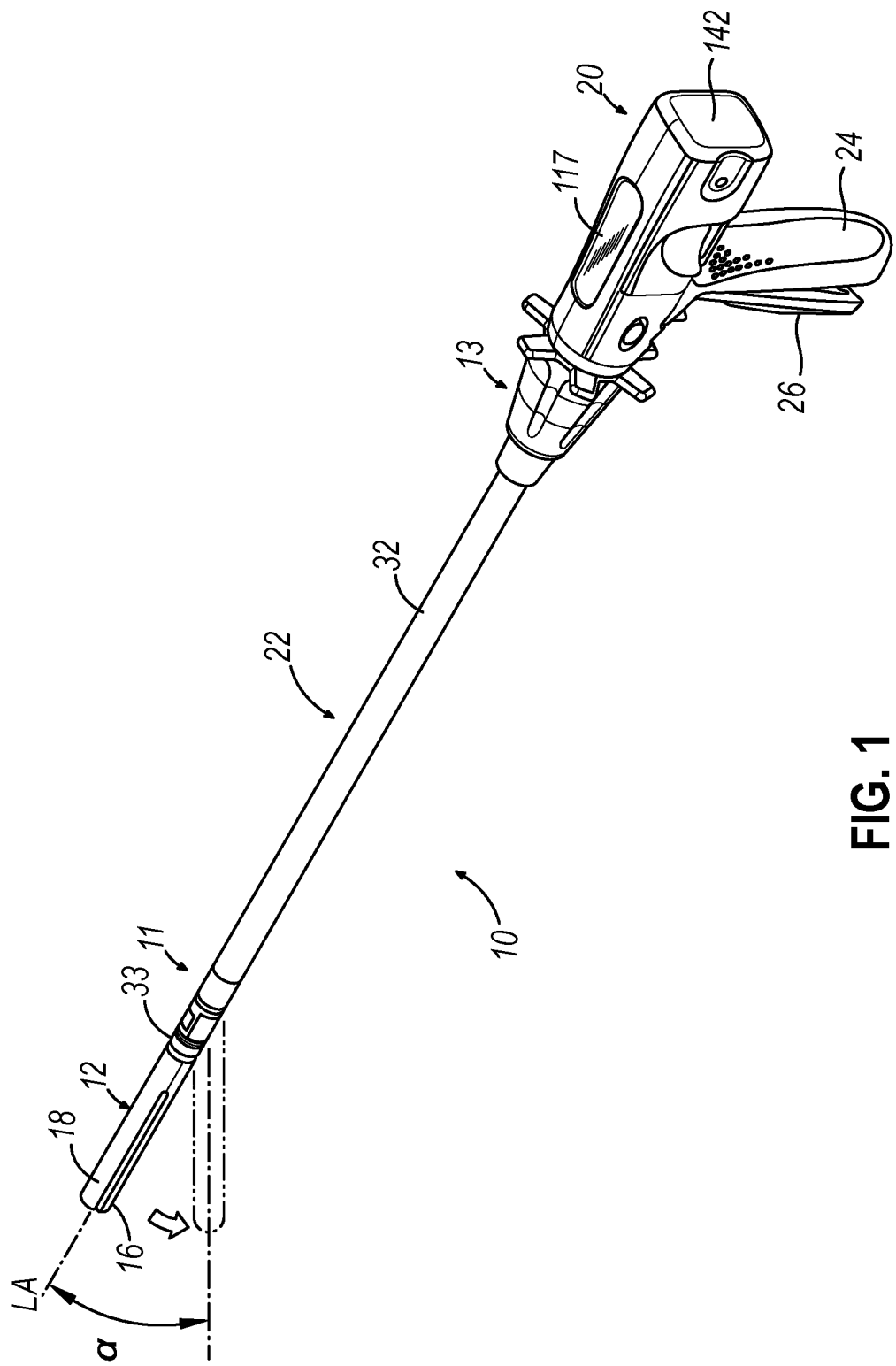
FIG. 1 depicts a perspective view of an illustrative articulating surgical stapling instrument.
Figure 2:
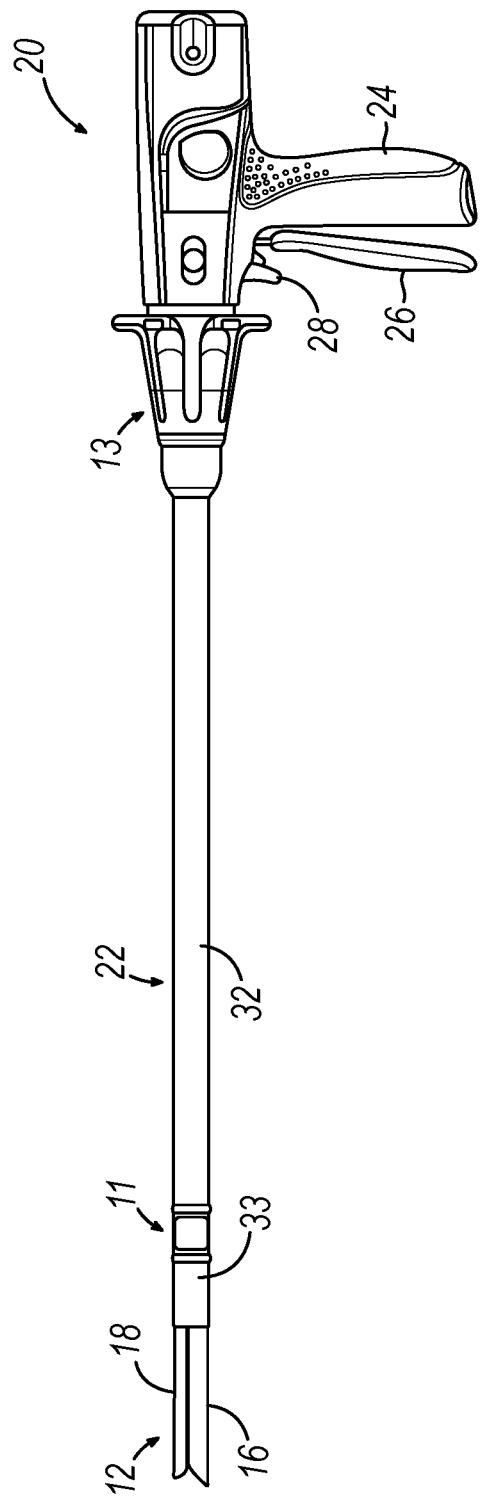
FIG. 2 depicts a side view of the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Illustrative Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20), for example via a motor (140) (not shown) housed within handle portion (20), to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
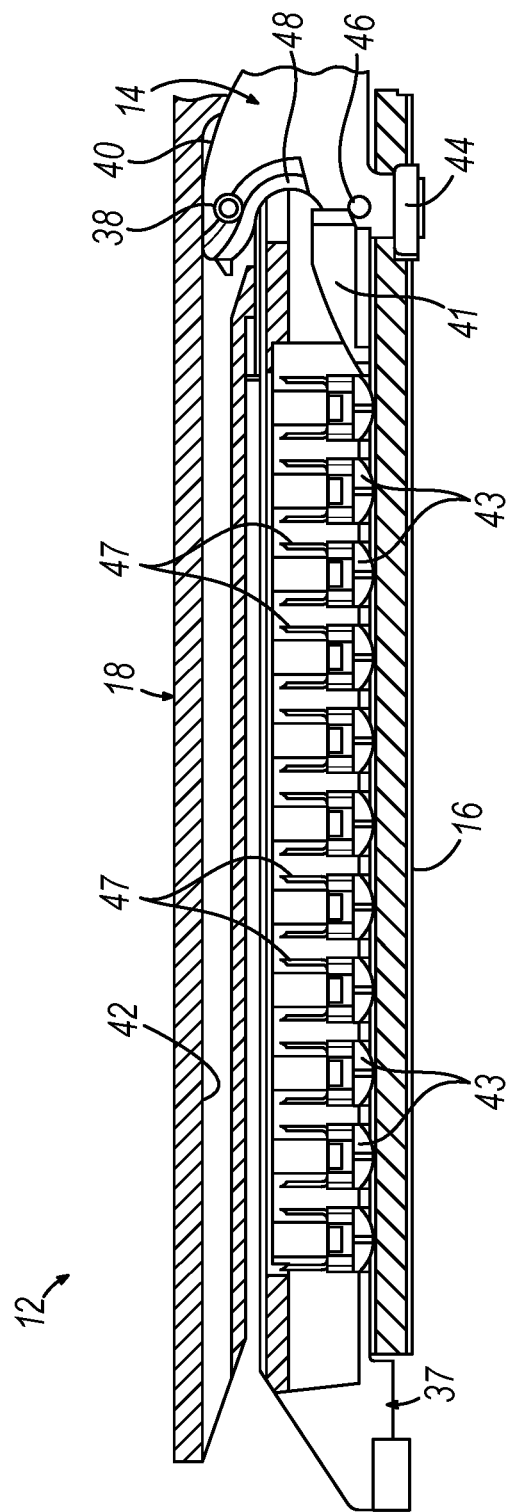
FIG. 4A depicts a side cross-sectional view of the end effector of FIG. 3, taken along line 4-4 of FIG. 3, with a firing beam of the end effector in a proximal position.
Figure 4B:
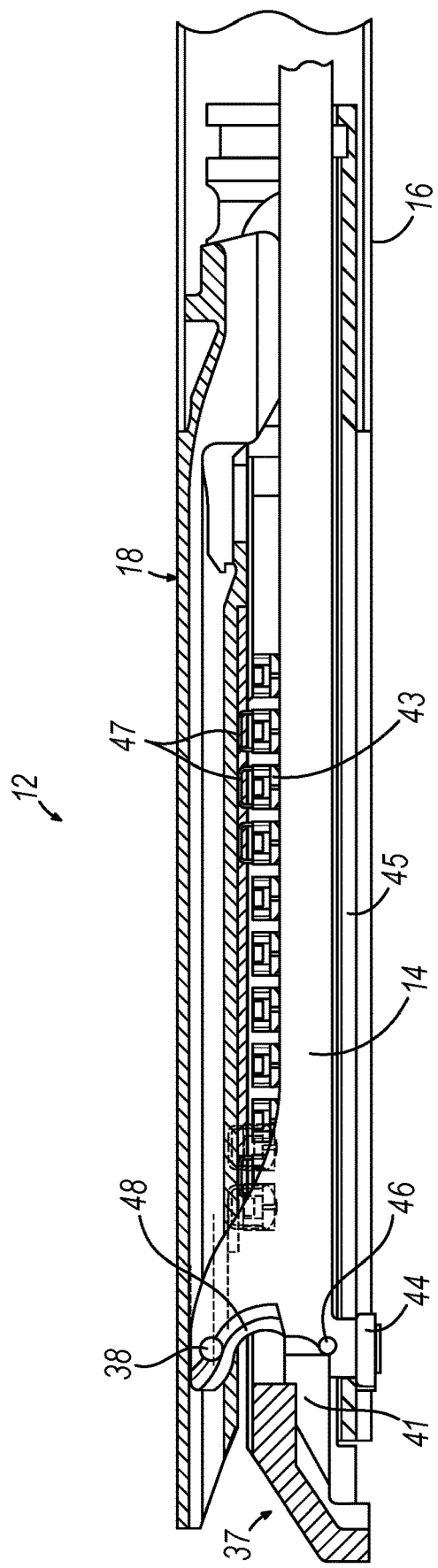
FIG. 4B depicts a side cross-sectional view of the end effector of FIG. 3, taken along line 4-4 of FIG. 3, with the firing beam in a distal position.

As seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
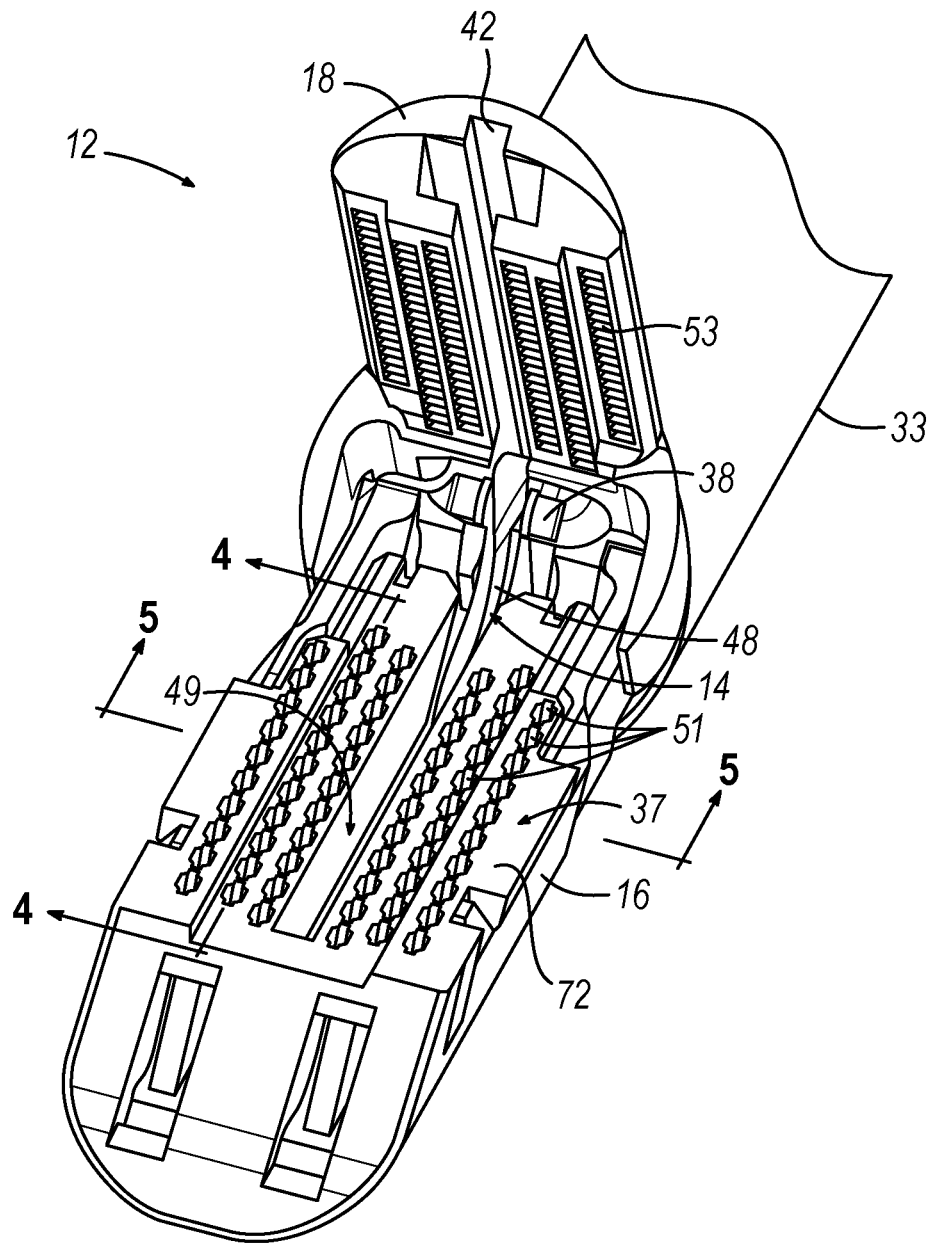
FIG. 3 depicts a perspective view of an opened end effector of the instrument of FIG. 1.
Figure 5:
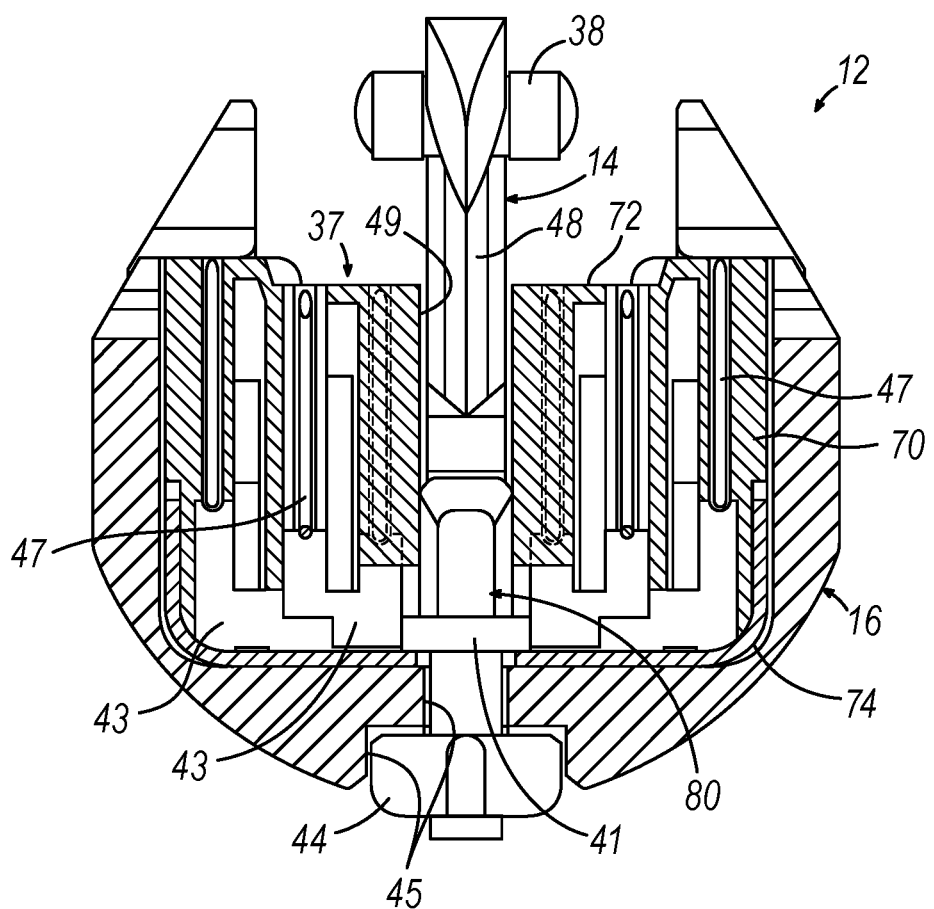
FIG. 5 depicts an end cross-sectional view of the end effector of FIG. 3, taken along line 5-5 of FIG. 3.
Figure 6:
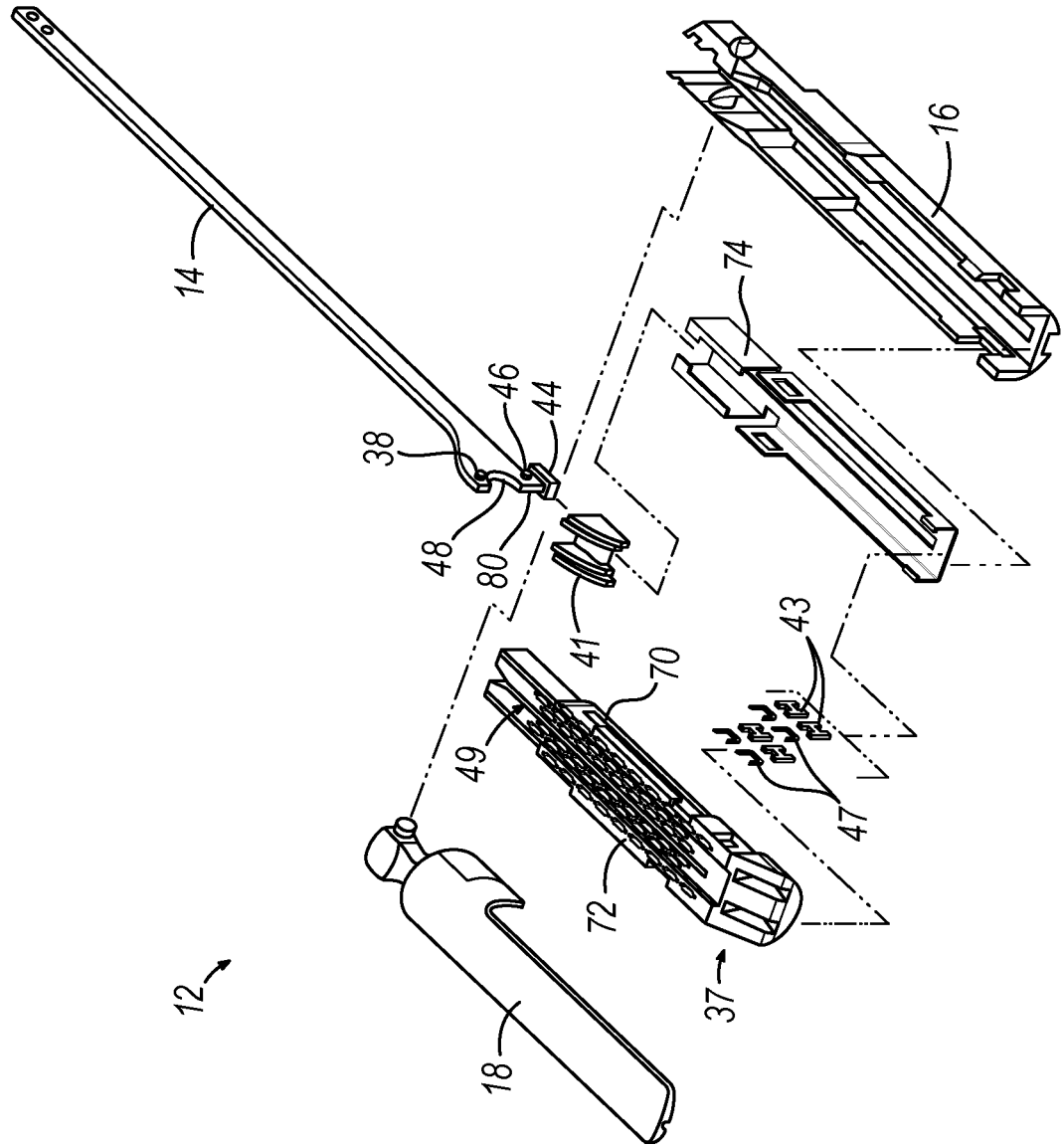
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As seen in FIGS. 5-6, staple cartridge (37) of this example includes a cartridge body (70), which presents an upper deck (72) and is coupled with a lower cartridge tray (74). As seen in FIG. 3, a vertical slot (49) is formed through part of staple cartridge (37). As also seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43) prior to firing of instrument (10) to discharge staples (47). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
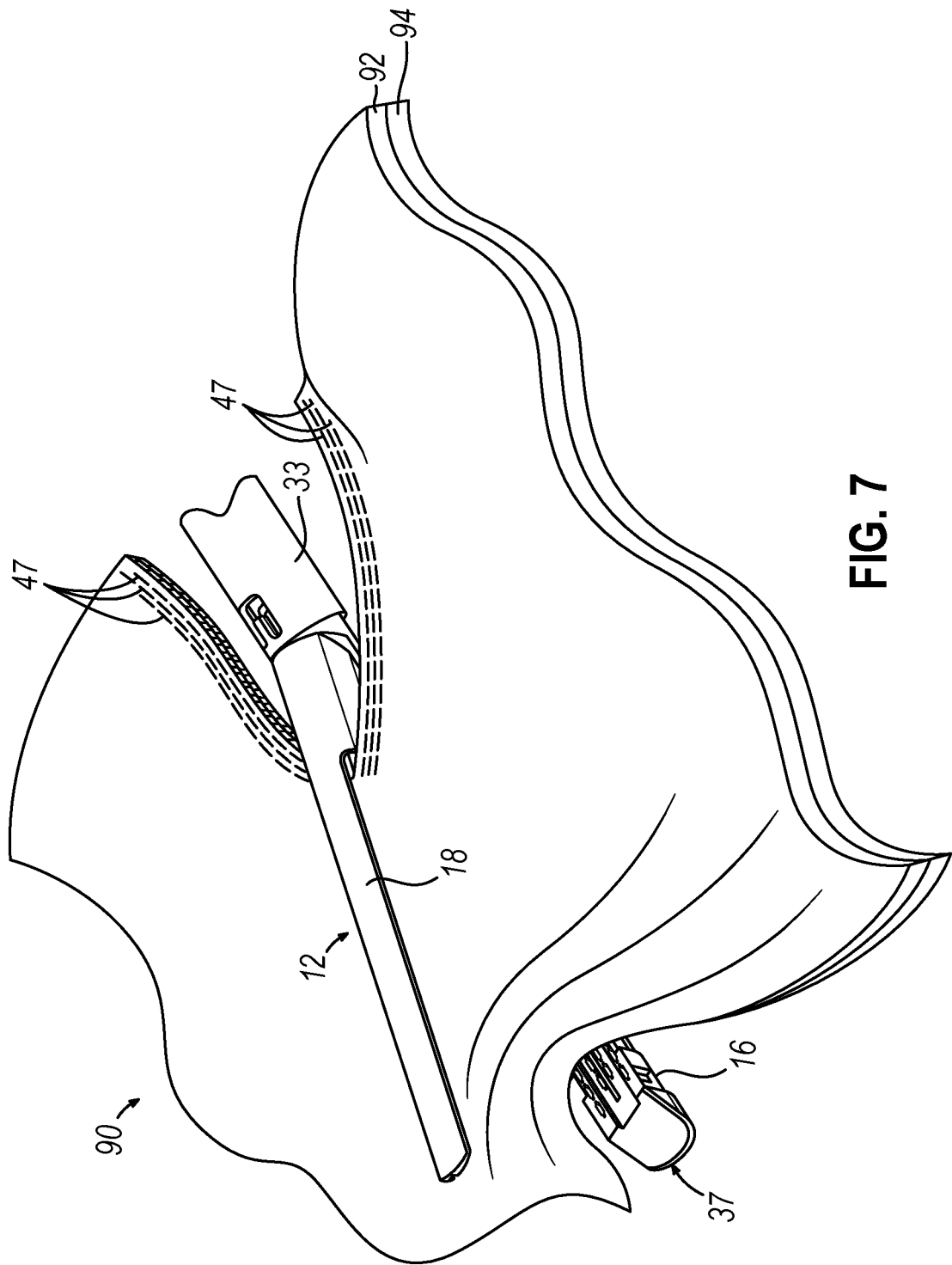
FIG. 7 depicts a perspective view of the end effector of FIG. 3, positioned at tissue and having been actuated once contacting the tissue.

FIG. 7 shows end effector (12) having been actuated through a single stroke through layers (92, 94) of tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In the present version, instrument (10) further includes an electric motor (not shown) housed within handle portion (20) that provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

In motorized versions of instrument (10), instrument (10) may also include a manual return switch, or "bail out switch," (not shown) positioned on or within handle portion (20), such as within or under a user-accessible panel or "bail out door" (not shown), the bail out switch being configured to enable the operator to quickly begin retracting firing beam (14) proximally during a firing stroke. In other words, the bail out switch may be manually actuated when firing beam (14) has only been partially advanced distally. Such a bail out switch may provide further functionality in accordance with at least some of the teachings of U.S. Pat. No. 9,622,746, incorporated by reference above.

Instrument (10) of the present example further includes a display screen (117) on an exterior of handle portion (20) such that display screen (117) is readily visible to a user. Display screen (117) may be configured to provide a visual indication to the user of one or more statuses of instrument (10), such as a remaining power level of a battery (142) (e.g., a removable battery pack), and/or various other conditions of instrument (10).

II. End Effector Features for Measuring Electrical Impedance of Tissue

In some instances, it may be desirable to configure end effector (12) of surgical stapling instrument (10) to sense at least one of a presence (including a longitudinal position of), an absence, or a characteristic of in vivo material, such as patient tissue, positioned between jaws (16, 18) during a surgical procedure. As used herein, the term "in vivo material" encompasses any material, biological or non-biological, that may be located within a body cavity of a patient in which a surgical procedure is being performed with instrument (10).

Described in greater detail below are various illustrative electrode arrays suitable for use with end effector (12), where each such electrode array includes one or more cooperating pairs of electrodes that are laterally opposed from one another and electrically coupled with an electrical energy source and configured to deliver bipolar radio frequency (RF) energy to in vivo material at relatively low, diagnostic levels (i.e., non-therapeutic RF energy, also referred to herein as an electrical signal). In particular, each cooperating pair of electrodes includes a first electrode configured to deliver an electrical signal to in vivo material positioned between end effector jaws (16, 18) and in contact with the electrodes, and a second electrode configured to receive the electrical signal after having passed through the tissue. In other versions of the illustrative examples described below, the surgical instrument may include a first electrode presented by the end effector and a second electrode located remotely from the end effector, where the first and second electrodes cooperate to direct a monopolar RF electrical signal through the in vivo material. In such versions, the second electrode may be in the form of an electrical grounding pad secured to the skin of the patient, for example as disclosed in any of the references incorporated by reference herein.

As described in greater detail below, FIGS. 8-13 show several illustrative electrode arrays each having one or more cooperating pairs of electrodes configured to transmit an RF electrical signal through in vivo material, such as tissue. While in each illustrative version the electrode array is shown and described as being integrated into a single end effector jaw, in other versions the electrode array may be integrated into both end effector jaws such that a given cooperating pair of electrodes includes a first electrode on a first end effector jaw and a second electrode on the second end effector jaw.

As described in greater detail below in connection with FIGS. 14-18, the electrodes of an electrode array may be electrically coupled with a tissue sensing circuit of compact size that is integrated into a component of end effector (12), such as lower jaw (16) or staple cartridge (37), and is configured to measure an electrical impedance of in vivo material positioned between and in contact with a given pair of electrodes. Based on this measured electrical impedance, the tissue sensing circuit may determine at least one of a presence of tissue in the in vivo material, an absence of tissue in the in vivo material, or a characteristic of a tissue that forms at least a part of the in vivo material. Instrument (10) may then take responsive action based on the impedance measurements and determination, which may include providing a notification to the operator. While the illustrative configurations described below are disclosed in connection with a surgical stapling instrument, it will be appreciated that such configurations may be applied to various other types of surgical instruments as well, such as surgical instruments operable to grasp tissue and/or treat tissue with ultrasonic energy and/or RF energy, for example.

A. Illustrative End Effector Electrode Array

Figure 8:
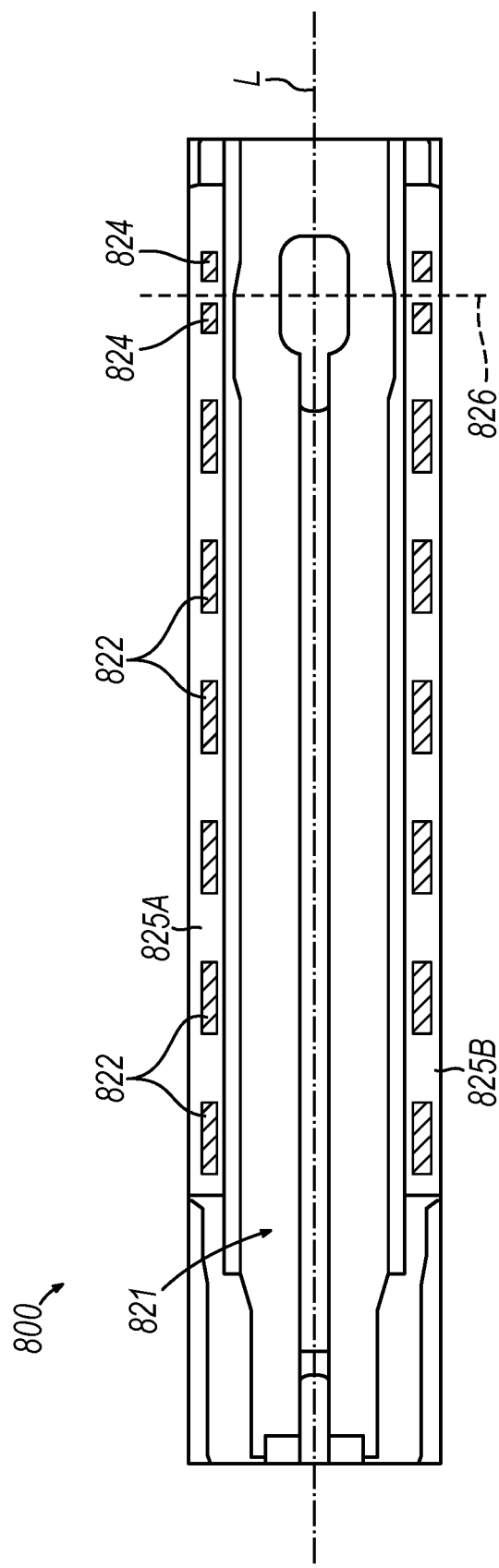
FIG. 8 depicts a top elevational view of another illustrative end effector jaw with an electrode array configured for use with the surgical stapling instrument of FIG. 1.

Referring now to FIG. 8, an illustrative electrode array (800) is depicted in accordance with at least one non-limiting aspect of the present disclosure. Although the electrode array (800) is depicted as a component of lower jaw (16) of end effector (12) of FIGS. 1-7, it shall be appreciated that the electrode array (800) may be implemented in a jaw of a variety of other types of surgical instruments. As shown in FIG. 8, an upper jaw (16) of the end effector (12) can define an elongate channel (821) that traverses a longitudinal axis (L) of the end effector (12). Specifically, the channel (821) can be defined by one or more side walls (825A, 825B) of lower jaw (16) that extend along the longitudinal axis (L) on opposing sides of the longitudinal axis (L). For example, the electrode array (800) may include eight pairs of electrodes (822, 824) each having a rectangular shape and constructed from titanium, where each electrode (822, 824) is configured to cooperate with a laterally opposed electrode (822, 824) to transmit an RF electrical signal through tissue positioned in contact with the two electrodes (822, 824). In other versions, the array (800) can include electrodes (822, 824) of varying numbers, geometries, and/or materials, depending on intended application and/or user preference. In further implementations, certain electrodes (824) of the array (800) may be configured differently relative to other electrodes (822). For example, certain electrodes (824) can be positioned about a cutline (826) and may be configured such that the electrodes (824) provide an increased resolution at either side of the cutline (826).

According to another non-limiting aspect of FIG. 8, the electrode array (800) could include one or more electrodes (822, 824) integrated into the side walls (825A, 825B) of the lower jaw (16) of the end effector (12). Specifically, each electrode (822, 824) may be over-mounted, or over-molded onto the walls (825A, 825B). Of course, other means of integration can be employed to a achieve a similar effect. In some implementations, certain electrodes (824) may be positioned about a cutline (826) of the end effector (12), such that those electrodes (824), when activated, can cut tissue about the cutline (826). In other versions, electrode array (800) may be integrated into upper jaw (18) of end effector (12).

Figure 9:
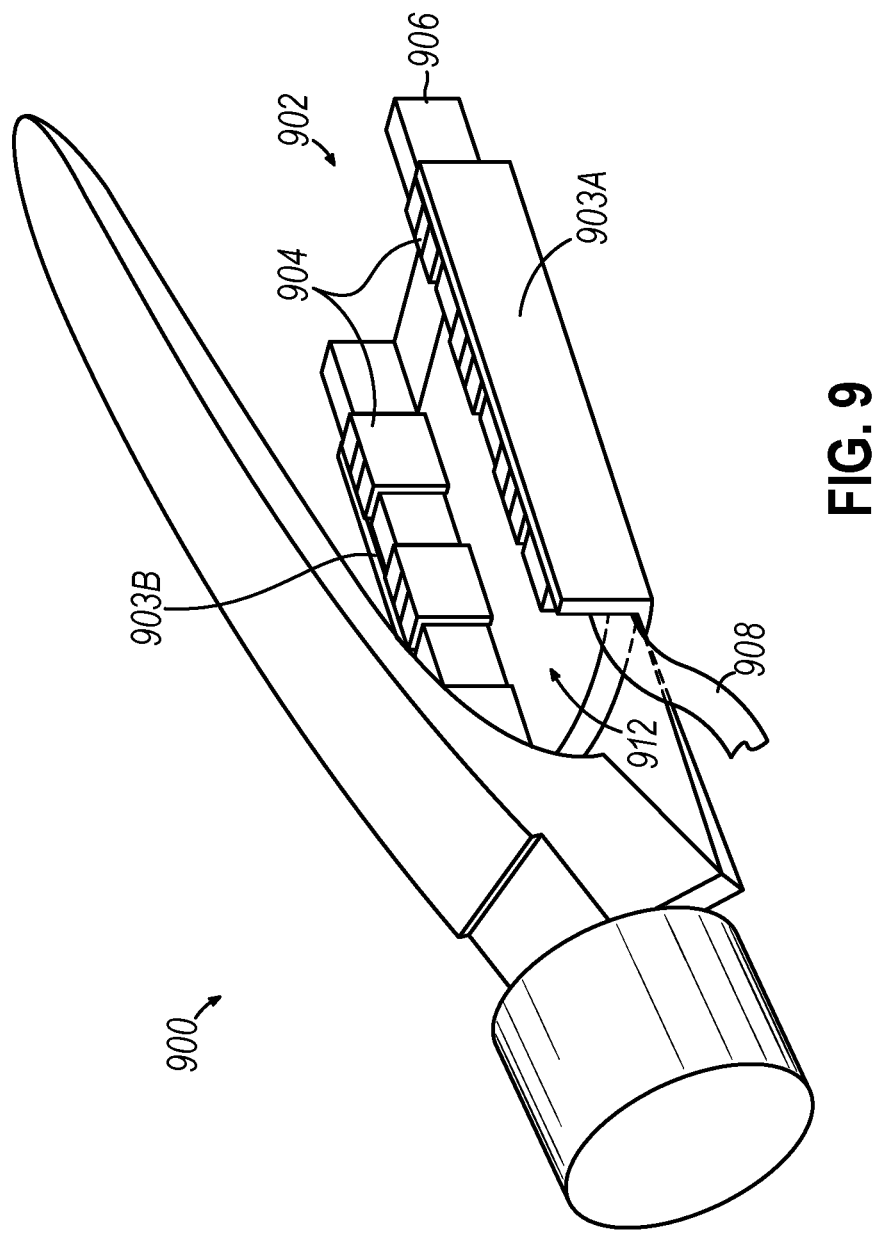
FIG. 9 depicts a perspective view of another illustrative end effector with an electrode array configured for use with the surgical stapling instrument of FIG. 1.

Referring now to FIG. 9, another end effector (900) is depicted in accordance with at least one non-limiting example of the present disclosure. According to some implementations, and as shown in FIG. 9, the end effector (900) may include an array of electrodes (904) mounted on a separate consumable (906) configured to be inserted within a channel (902) defined by the sidewalls (903A, 903B) of the end effector (900), where each electrode (904) is configured to cooperate with a laterally opposed electrode (904) to transmit an RF electrical signal through tissue positioned in contact with the two electrodes (904). Channel (902) and sidewalls (903A, 803B) may be configured to accommodate the separate consumable (906). For example, the sidewalls (903A, 903B) may include an interior surface composed of a conductive material, such that the conductive material is placed into electrical communication with the electrodes (904) when the separate consumable is inserted into the channel (902). Additionally, or alternately, the channel may include one or more electrical contacts configured to place the electrodes (904) into electrical communication with a flexible conductor (908) capable of carrying multiplexed signals, wherein the flexible conductor (908) traverses through the channel (902).

Thus, in some implementations, and as shown in FIG. 9, array of electrodes (904) may be attached to a separate consumable (906) and thus, selectively clipped into the channel (902). In this way, a single end effector (900) can be configured to selectively accommodate numerous separate consumables (906), wherein each separate consumable (906) can include a different array of electrodes (904) of varying configurations. Furthermore, the separate consumable (906) can define a second channel (912) configured to accommodate a cartridge for the surgical operation (e.g., a staple cartridge, an electrosurgical cartridge, etc.). Accordingly, various combinations of separate consumables (906) and cartridges can be used by the same end effector (900). Moreover, the electrodes (904) can receive and send signals via the flexible conductor (908), which can be used to generate insights per the previously disclosed techniques, regardless of the cartridge type loaded into the end effector (900). According to some non-limiting aspects, the flexible conductor (908) can be routed through the end effector (900) and surgical instrument.

Figure 10A:
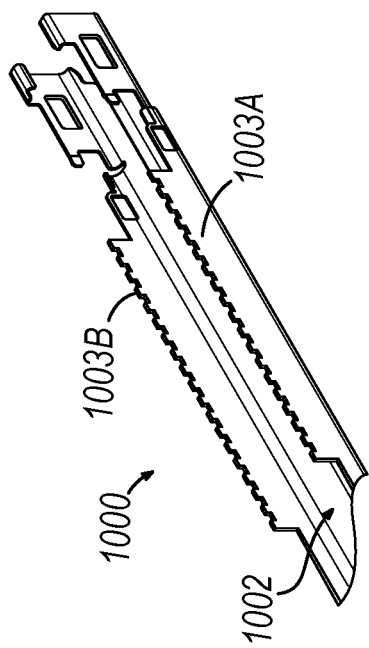
FIG. 10A depicts a perspective view of a portion of another illustrative end effector with an electrode array configured for use with the surgical stapling instrument of FIG. 1.
Figure 10B:
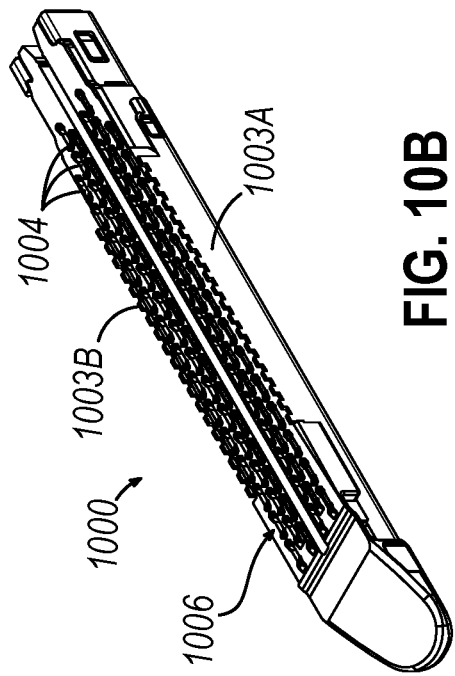
FIG. 10B depicts a perspective view of a staple cartridge configured for use with the end effector portion of FIG. 10A.
Figure 10C:
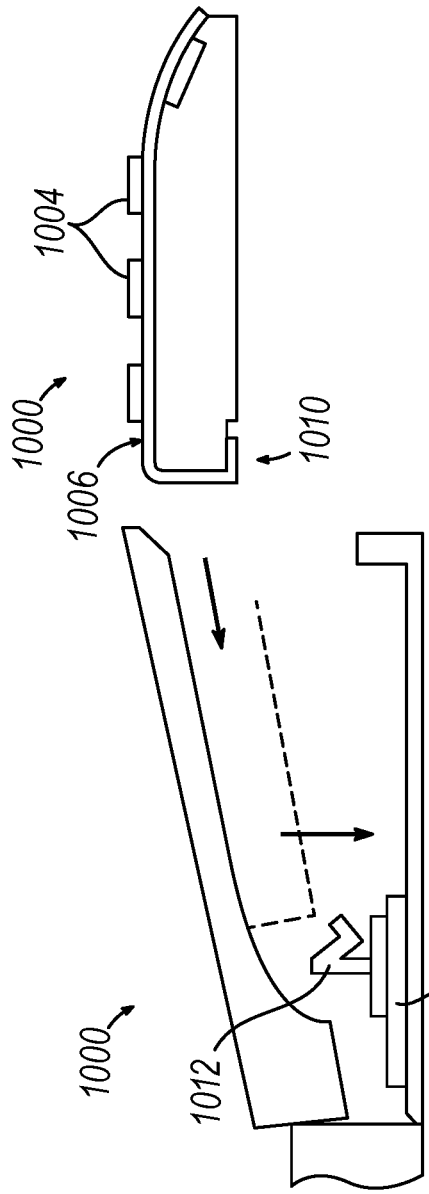
FIG. 10C depicts a side elevational view of another illustrative end effector that incorporates the end effector portion of FIG. 10A and the staple cartridge of FIG. 10B.

Referring now to FIGS. 10A-10C, another end effector (1000) is depicted in accordance with at least one example of the present disclosure. In some implementations, and as shown, end effector (1000) may accommodate a cartridge (1006) configured to perform a surgical operation (e.g., a staple cartridge, an electrosurgical cartridge, etc.), and an array of electrodes (1004) can be disposed on the cartridge (1006), itself. Each electrode (1004) is configured to cooperate with a laterally opposed electrode (1004) to transmit an RF electrical signal through tissue positioned in contact with the two electrodes (1004). In specific reference to FIGS. 10A-10B, sidewalls (1003A, 1003B) of the end effector (1000), which in this case are defined by a tray of cartridge (1006) similar to tray (74), can once again define a channel (1002), and the channel can be configured to accommodate a body of the cartridge (1006). The end effector (1000) may further include a flexible conductor (1008) capable of carrying multiplexed signals, wherein the flexible conductor traverses through the channel (1002). In some implementations, the flexible conductor (1008) may be routed through the end effector (1000) and surgical instrument in a method similar to those described in reference to the end effector (900) of FIG. 9.

For example, the sidewalls (1003A, 1003B) may include an interior surface composed of a conductive material, such that the conductive material is placed into electrical communication with the electrodes (1004) when the separate consumable is inserted into the channel (1002), as illustrated in FIG. 10C. Alternately, the channel can include one or more electrical contacts configured to place the electrodes (1004) into electrical communication with a flexible conductor (1008) capable of carrying multiplexed signals, wherein the flexible conductor (1008) traverses through the channel (1002).

In a further implementation, and as shown in FIG. 10C, an insertion of the cartridge (1006) into the end effector (1000) is depicted in accordance with at least one non-limiting aspect of the present disclosure. According to the non-limiting aspect of FIG. 10C, the end effector (1000) may include a conductive element (1012) configured to electrically interface with a corresponding conductive element (1010) on the cartridge (1006). The conductive elements (1010), (1012) can further be configured for multiplexed signal transmission, such that multiplexed signals transmitted through the flexible conductor (1008) of the end effector (1000) can be communicated to and from each electrode (1004) of the array, positioned on the cartridge (1006). In a further implementation, the array of electrodes (1004) may be integrated onto cartridge (1006), which can be a consumable. The electrodes (1004) can be electrically integrated within the cartridge (1006) via a multiplexing integrated circuit inside the cartridge and electrical connections between the conductive elements (1010, 1012). Because the cartridge (1006) can include the multiplexing electronics, the conductive elements (1010, 1012) must interface between the end effector (1000) and the cartridge (1006) can be simplified.

Figure 11B:
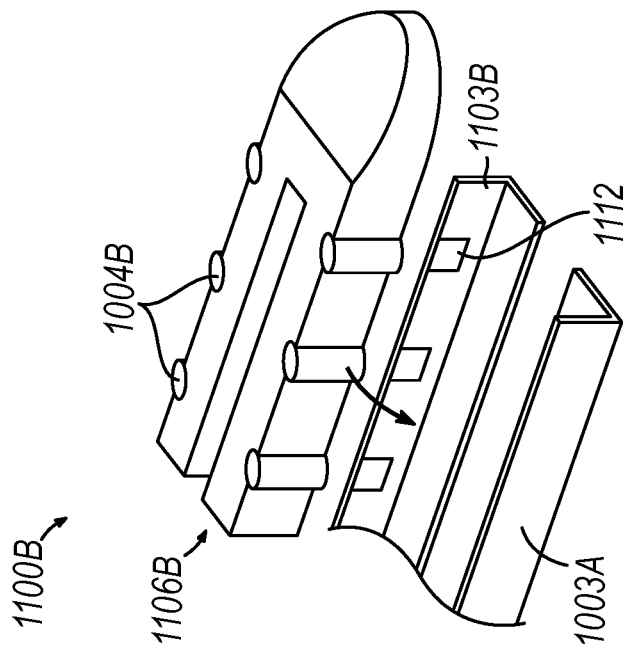
FIG. 11B depicts a perspective view of another illustrative end effector with an electrode array configured for use with the surgical stapling instrument of FIG. 1.
Figure 11A:
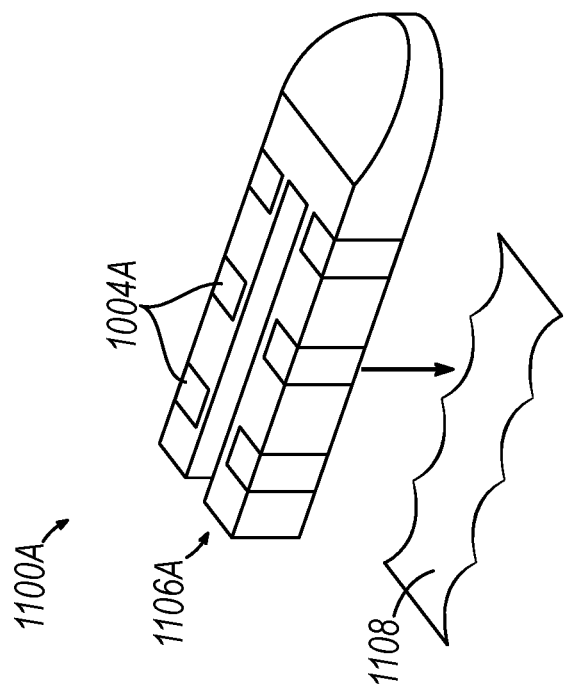
FIG. 11A depicts a perspective view of another illustrative end effector with an electrode array configured for use with the surgical stapling instrument of FIG. 1.

Referring now to FIG. 11A, another end effectors (1100A) is depicted in accordance with at least one non-limiting aspect of the present disclosure. End effector (1100A) may be configured to accommodate a hybrid cartridge (1106A) wherein an array of electrodes (1104A) are positioned on the cartridge (1106A). Each electrode (1104A) is configured to cooperate with a laterally opposed electrode (1104A) to transmit an RF electrical signal through tissue positioned in contact with the two electrodes (1104A). Each electrode (1104A) may be configured for electrical communication with a flexible conductor (1108) capable of carrying multiplexed signals. In another implementation, when the cartridge (1106A) is installed within the end effector (1100A), a flexible conductor (1108) may traverse through a channel defined by the end effector (1100A) and may be routed through the end effector (1100A) and surgical instrument in a method similar to those described herein.

In reference to FIG. 11B, a similar, albeit subtly different, end effector (1100B) is depicted in accordance with at least one non-limiting aspect of the present disclosure. Notably, the array of electrodes (1104B) are different than the electrodes (1104A) of FIG. 11A. As such, a plurality of conductive elements (1112) that correspond to each electrode (1104B) are disposed in each wall (1103A, 1103B) of the end effector (1100B). Accordingly, each electrode (1104B) of the array can receive an intended signal from the multiplexed signals traversing the flexible conductor (1108).

It should be appreciated that, in some implementations, as shown in FIGS. 11A-11B, the array of electrodes (1104A, 1104B) may be positioned on the cartridge (1106A, 1106B), which can be electrically configured with one or more electrical surfaces (e.g., metal plating, metal pieces bent around the sides, vias through the cartridge, etc.) for an intended connection of each electrode (1104A, 1104B) to an appropriate portion of the flexible conductor (1108). Accordingly, multiplexing takes place in the end effector (1100A, 1100B) but each electrode (1104A, 1104B) still receives the appropriate signal via the electrical connections.

Figure 12:
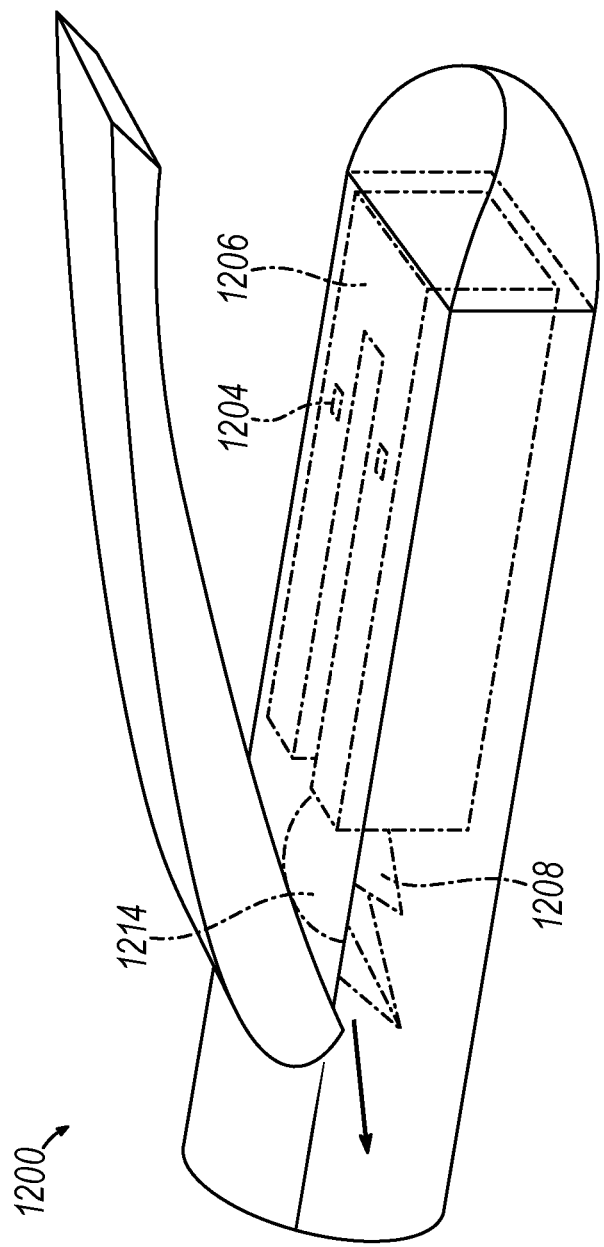
FIG. 12 depicts a perspective view of an illustrative wireless end effector with an electrode array configured for use with the surgical stapling instrument of FIG. 1.

Referring now to FIG. 12, another end effector (1200) is depicted in accordance with at least one non-limiting example of the present disclosure. Similar to the end effectors (1100A, 1100B) of FIGS. 11A-11B, the array of electrodes (1204) can be integrated on the cartridge (1206), itself, where each electrode (1204) is configured to cooperate with a laterally opposed electrode (1204) to transmit an RF electrical signal through tissue positioned in contact with the two electrodes (1204). Multiplexing, however, can occur either within the cartridge (1206) or end effector (1200) via a flexible conductor (1208) capable of carrying multiplexed signals. Regardless, the end effector (1200) of FIG. 12 can further include a wireless communication module (1214) configured to transmit and receive multiplexed signals to and from a control circuit and/or a surgical hub wirelessly via an infrastructure network (e.g., WiFi®, cellular, etc.) or an ad hoc network (e.g., Bluetooth®, Near Field Communications, RFID, etc.).

Accordingly, the wireless communication module (1214) can serve as a communication interface between the end effector (1200) and the surgical hub and/or control circuit, thereby eliminating the need for the routing described in reference to FIGS. 10 and 11. It shall be appreciated that a wireless communication module (1214) can be similarly applied to any of the surgical instruments and/or end effectors disclosed herein, thereby simplifying—and in some aspects, eliminating—the routing of the flexible conductors disclosed herein.

Figure 13:
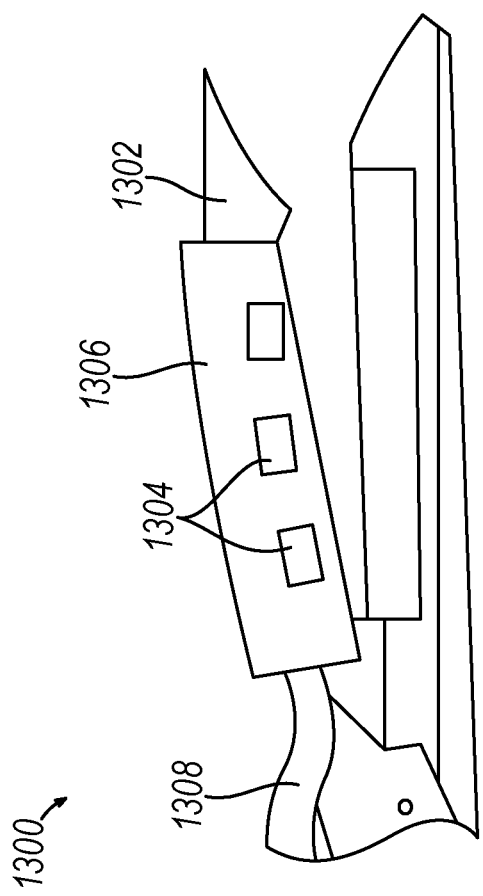
FIG. 13 depicts a partial perspective view of another illustrative end effector with an electrode array configured for use with the surgical stapling instrument of FIG. 1.

Referring now to FIG. 13, another end effector (1300) is depicted in accordance with at least one non-limiting example of the present disclosure. As shown, the end effector (1300) may include a first jaw and a second jaw. For example, the second jaw can be configured as an anvil of the end effector (1300) and a separate consumable (1306) can be configured to be selectively coupled to the second jaw. Whereas the separate consumable (906) of FIG. 9 was shown as coupled to a bottom jaw of the end effector (900) of FIG. 9, the separate consumable (1306) can be coupled to the second, or top, jaw (1302) of the end effector (1300). Nonetheless, the array of electrodes (1304) can be coupled to the separate consumable (1306) and, when coupled to conductive elements on the second jaw (1302), electrically coupled to a flexible conductor (1308). Each electrode (1304) is configured to cooperate with a laterally opposed electrode (1304) to transmit an RF electrical signal through tissue positioned in contact with the two electrodes (1304). The flexible conductor (1308) can be capable of carrying multiplexed signals, wherein the flexible conductor (1308) traverses through the end effector (1300) and surgical instrument in a method similar to those described with reference to FIGS. 9-11. Alternately, the wireless implementation of FIG. 12 can be employed to transmit signals to and from the array of electrodes (1204).

In alternative versions of any of the illustrative electrode arrays described above, each pair of laterally opposed electrodes arranged along the length of end effector may be electrically isolated from one another and may be configured to communicate independently with a controller of the surgical instrument. Based on electrical impedance readings associated with the various different pairs of electrodes, the controller may determine a longitudinal position relative to the end effector of tissue located between the end effector jaws.

B. Illustrative Tissue Sensing Circuit

Figure 14:
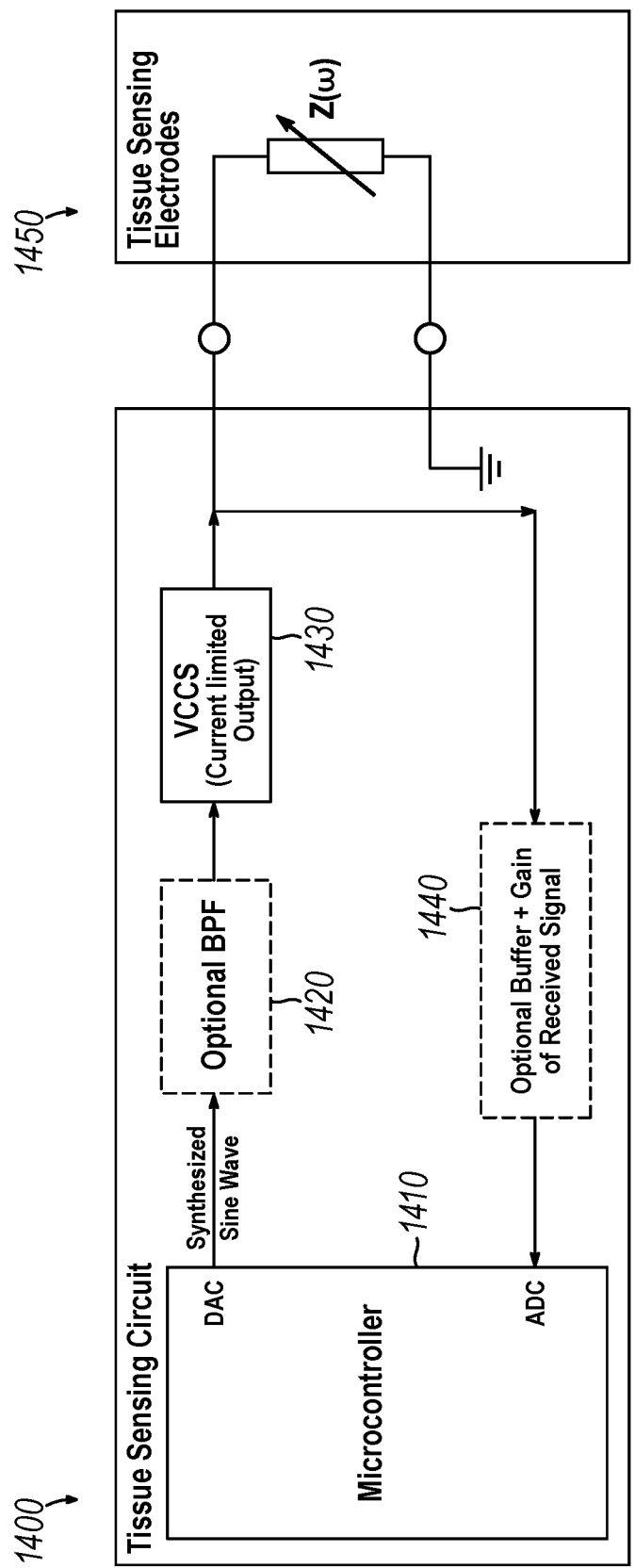
FIG. 14 depicts a diagrammatic view of an illustrative microcontroller configured for use with the surgical stapling instrument of FIG. 1.
Figure 15:
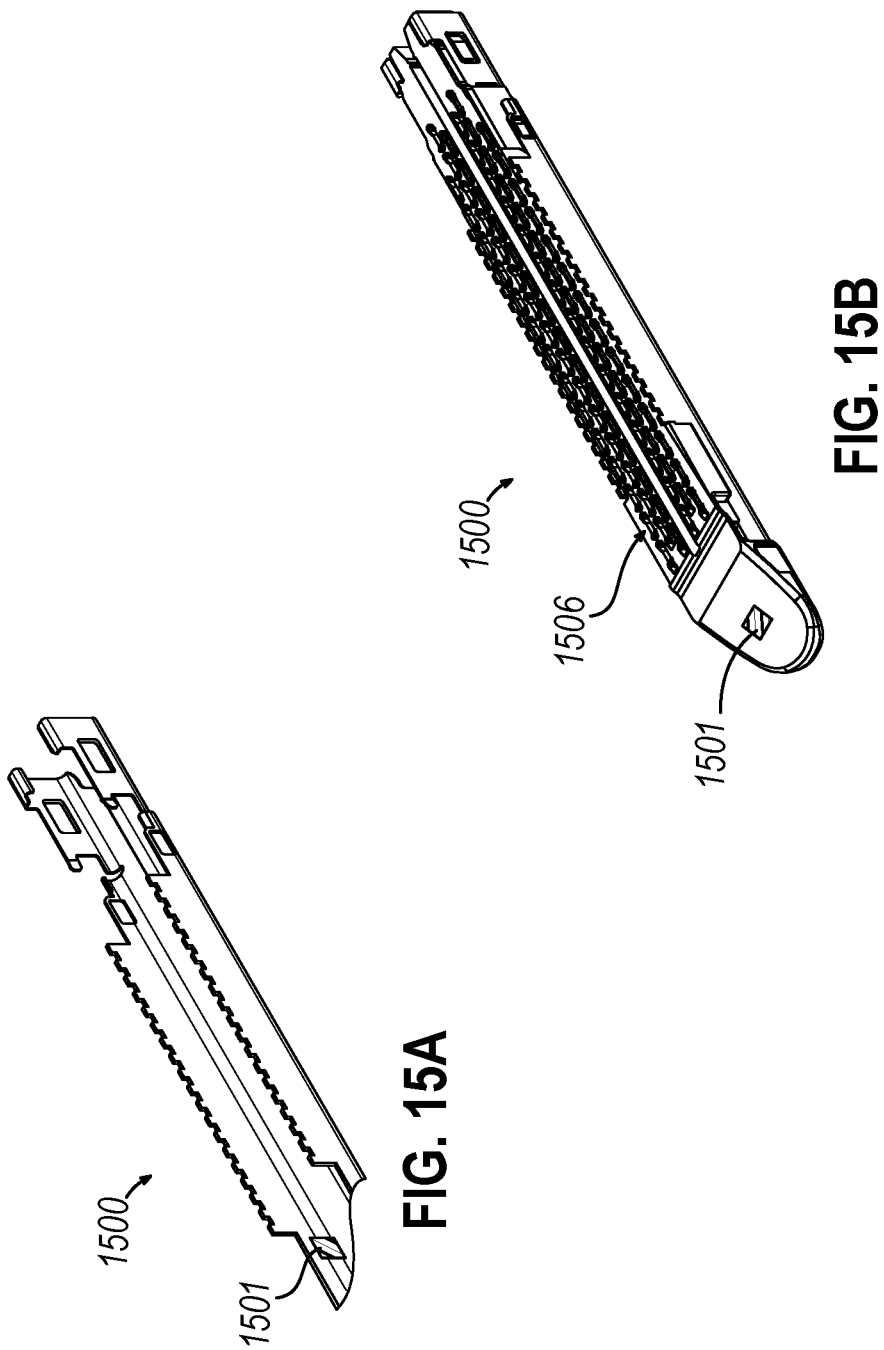
FIG. 15A depicts a perspective view of an illustrative end effector jaw having a microcontroller and configured for use with the surgical stapling instrument of FIG. 1.
FIG. 15B depicts a perspective view of an illustrative staple cartridge having a microcontroller and configured for use with the surgical stapling instrument of FIG. 1.

FIG. 14 shows a tissue sensing circuit (1400) coupled to one or more tissue sensing electrodes (1450), such as two or more pairs of electrodes (1450) where each pair is configured to deliver bipolar RF energy to tissue. Electrodes (1450) may be integrated into a surgical instrument effector, such as end effector (12), and may be operable in any of the illustrative ways disclosed above. As shown, the tissue sensing circuit (1400) may include various components. For example, the tissue sensing circuit (1400) may include a digital microcontroller (1410) that is configured to synthesize an output sine wave signal with a fixed fundamental frequency ($f_c$) through a Digital to Analog Converter port. The tissue sensing circuit (1400) may also include an optional band-pass-filter (1420) that may improve the sine wave signal by removing undesirable impurities. The tissue sensing circuit (1400) may also include a voltage-controlled current source (VCCS) (1430), which translates the signal to a current-limited incidental output, which ensures patient-safety) to tissue sensing electrodes (1450). An Op-Amp (1440) may also be present in the tissue sensing circuit (1400) in order to add gain to the returning signal from the electrodes.

In some implementations, and as shown in FIG. 14, microcontroller (1410) may recreate or act as an analog circuit. Thus, the microcontroller (1410) may be equipped with, have access to, or comprise an advanced embedded analog, mix-signal, and Digital Signal Processing (DSP) capabilities. It should be understood that although various microcontroller configurations are discussed herein that any feasible microcontroller may be used. By way of non-limiting example, microcontrollers STM32F3 and/or STM32G4 should be sufficient to perform the methods disclosed herein.

Referring now to FIGS. 15A and 15B, portions of another end effector (1500) are depicted in accordance with at least one implementation of the present disclosure. As shown, end effector (1500) may accommodate a cartridge (1506) configured to perform a surgical operation (e.g., a staple cartridge, an electrosurgical cartridge, etc.), and an array of electrodes can be disposed on the cartridge (1506), itself. In some implementations, and as shown schematically in FIG. 15A, a tissue sensing circuit (1501), which may be similar to tissue sensing circuit (1400) of FIG. 14, may reside on or be recessed within an interior surface of a lower jaw (16) of the end effector (1500), such as a side wall or a floor of lower jaw (16) such that tissue sensing circuit (1501) is covered by cartridge (1506) when seated within lower jaw (16). In this implementation, because the tissue sensing circuit (1501) is permanently affixed to, or housed within, the end effector (1500) (specifically, jaw (16)), it is not discarded with cartridge (1506) between firings of end effector (1500) and thus may be reused for multiple firings, which may save on cost for the user.

Alternatively, in some implementations, such as shown in FIG. 15B, the tissue sensing circuit (1501) may reside on or be housed within the cartridge (1506) that is inserted into the end effector (1500). For instance, as shown schematically, tissue sensing circuit (1501) may be embedded within a tapered distal end of a body of cartridge (1506). In this implementation, because the tissue sensing circuit (1501) is permanently affixed to, or housed within, the cartridge (1506), it is discarded with cartridge (1506) after cartridge (1506) is fired and removed from end effector (1500). Various other implementations may exist regarding the placement of the tissue sensing circuit (1501) to enable a single use or multiple uses. In a further implementation, the tissue sensing circuit (1501) may be provided in both end effector jaw (16) and in cartridge (1506), which may provide redundancy in case of failure for malfunction.

C. System Operation and Capability

The systems discussed herein and shown in FIGS. 1-15B provide for a surgical stapler instrument (10) that is configured to clamp tissue using an end effector (12). Once securely clamped, electrodes (e.g., the electrodes shown in FIGS. 8-13) in the end effector (12) apply a non-therapeutic (i.e., low voltage) waveform to the tissue. The returning waveform is then evaluated to measure and/or calculate (e.g., using the microcontroller of FIG. 14) the impedance of the tissue. More specifically, the system via one or more sub-circuits will provide non-therapeutic energy to the extra-cellular and intracellular fluid present within a given (e.g., clamped) region of tissue to determine a phase and a magnitude of the impedance of the tissue within jaws. The system may then relay information associated with the tissue, such as, for example, tissue type, tissue phase, tissue margin, and the like. Using this associated information, the system can not only verify that the proper tissue is clamped between the jaws but can also determine if any non-tissue material is present between the jaws.

Figure 16:
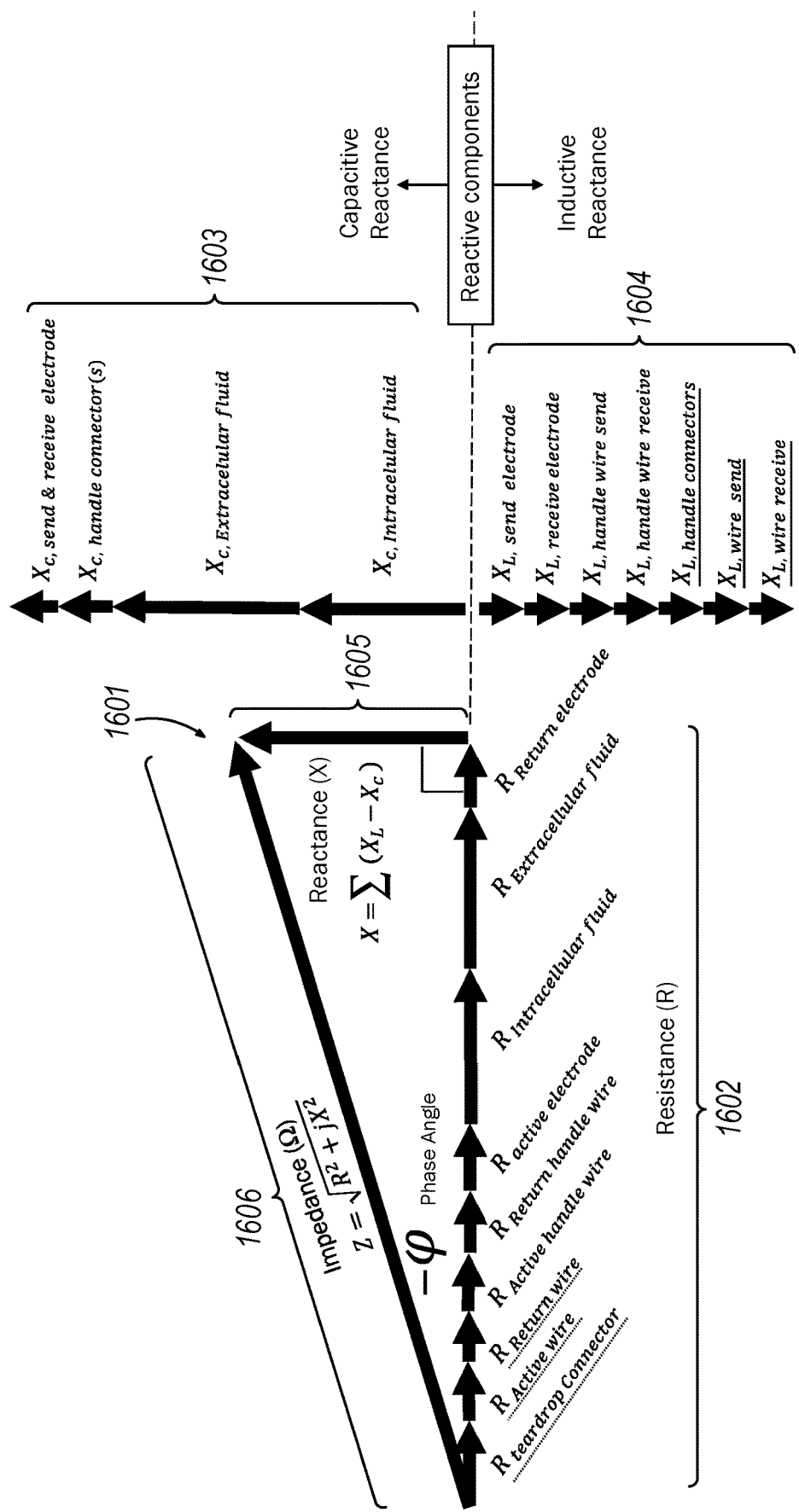
FIG. 16 depicts a diagrammatic view of an illustrative example impedance triangle.
Figure 17:
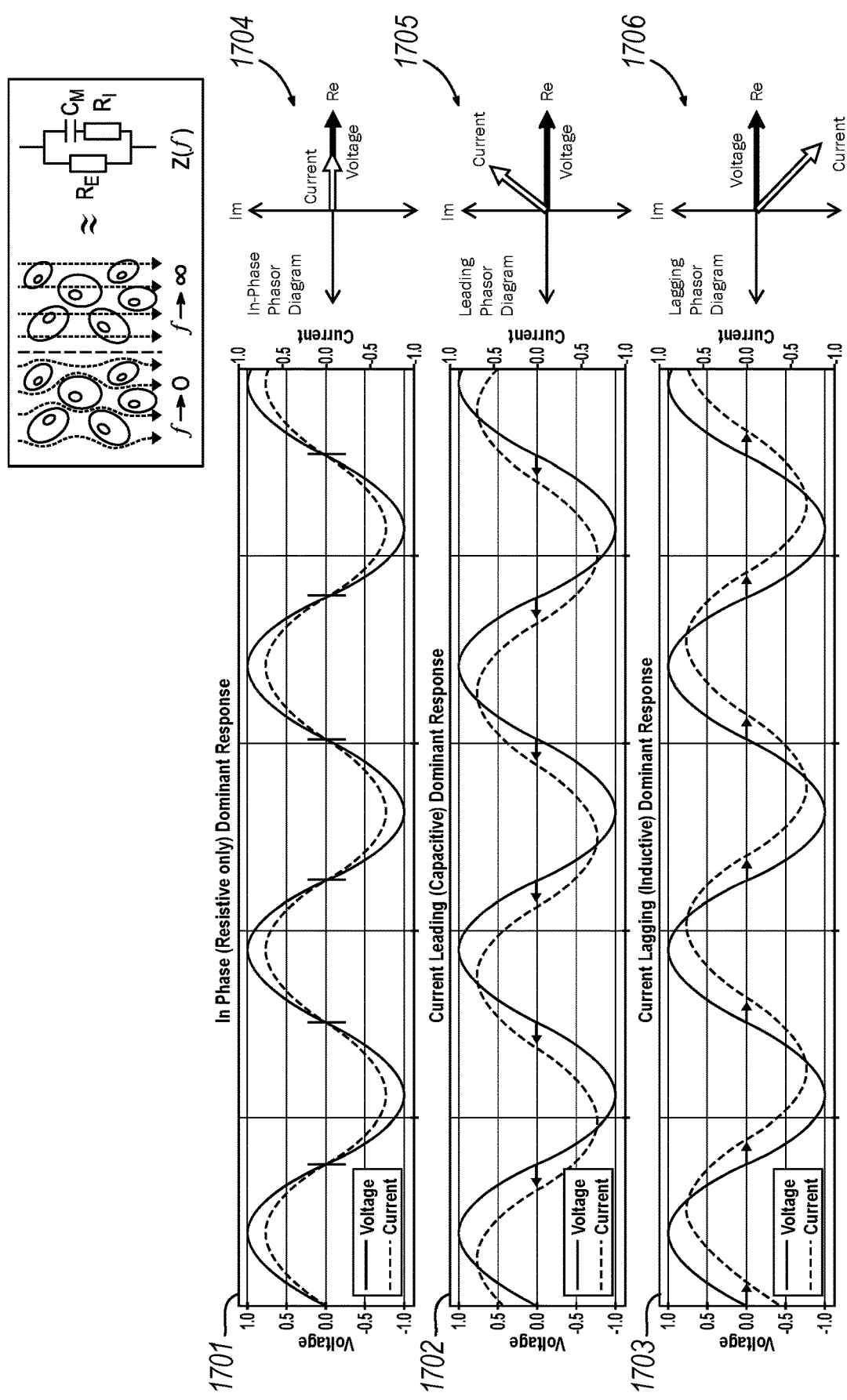
FIG. 17 depicts a diagrammatic view of a set of illustrative example waveforms generated and measured by the surgical stapling instrument of FIG. 1.

FIG. 16 shows an illustrative impedance triangle (1601) that may be implemented by tissue sensing circuit (1400) to determine an electrical impedance of tissue placed in contact with a pair of electrodes of a surgical instrument end effector, such as end effector (12). As would be understood by one skilled in the art, human tissues may tend to be capacitive in nature, while wires, tool, staples, implants, etc. may tend to be inductive in nature. Thus, as can be seen by the illustrative impendence triangle (1601), the "resistance" (1602) of each object in the circuit is measured using the electrodes. The system can also determine the "capacitive reactance" (1603) of each object in the circuit and the inductive reactance (1604) of each object in the circuit (1400). As discussed above, and clearly shown in FIG. 16, the electrodes (e.g., the electrodes shown in FIGS. 8-14), via the microcontroller, send and receive electrical signals to and from the patient tissue. As should be understood by one of ordinary skill in the art, the extracellular fluid, and the intracellular fluid of a patient have capacitive reactance (1603). The "reactance" (1605) can then be calculated by determining the difference between the capacitive reactance and the inductive reactance using:

$X = \Sigma(X_L - X_C)$, where $X$ is total reactance, $X_L$ is inductive reactance, and $X_C$ is capacitive reactance. Equation 1:

As shown in FIG. 16, the "impedance" (1606) can then be determined using:

$Z = \sqrt{R^2 + jX^2}$, where $Z$ is impedance, $R$ is resistance, and $jX$ is equal to the square of the difference between inductive reactance and capacitive reactance (i.e., $(X_L - X_C)^2$). Equation 2:

FIG. 17 shows a set of illustrative example waveforms that may be generated and measured by tissue sensing circuit (1400) to determine the phase of the current and voltage of the circuit, as discussed herein. As would be understood by one skilled in the art, if a circuit only contains resistive items, the current and voltage will remain in phase such as shown in graph (1701) and phasor diagram (1704). Alternatively, if the circuit has capacitive objects, or more capacitive than inductive, the voltage wave will lead the current wave such as shown in graph (1702) and phasor diagram (1705). Finally, if the circuit has inductive objects, or more inductive objects than capacitive objects, the voltage will lag behind the current, such as shown in graph (1703) and phasor diagram (1706). As discussed above and shown in FIG. 16, human tissue tends to be capacitive in nature, while wires, tool, staples, implants, etc. may tend to be inductive in nature.

Thus, if the measurement of the current and voltage result in a current leading waveform (1702), it indicates that the material between the electrodes is "capacitive" and thus falls into the category of tissue or fluid (e.g., 1603). Alternatively, if the measurement of the current and voltage result in a current lagging waveform (1703), it indicates that the material between the electrodes is "inductive" and is thus not tissue or fluid (e.g., 1603). Accordingly, as discussed herein the electrodes (e.g., 1450) send and receive electrical signals to and from the end effector, which is believed to be in contact with patient tissue. The waveforms are then analyzed by the tissue sensing circuit (1400) to determine if the current is leading or lagging the voltage (e.g., 1702 vs 1703), which can then be used to confirm what is in contact with the electrodes.

As discussed herein, the system may pass a non-therapeutic waveform through a portion of patient tissue to help identify the type of tissue as well as any foreign objects. Thus, in some versions, the system may pass waveforms of varying frequency (e.g., in series and/or parallel) to improve the accuracy of the determination. Accordingly, in some implementations, multiple waveforms of various frequencies may be added or summed together to create a multi-sine waveform.

Figure 18:
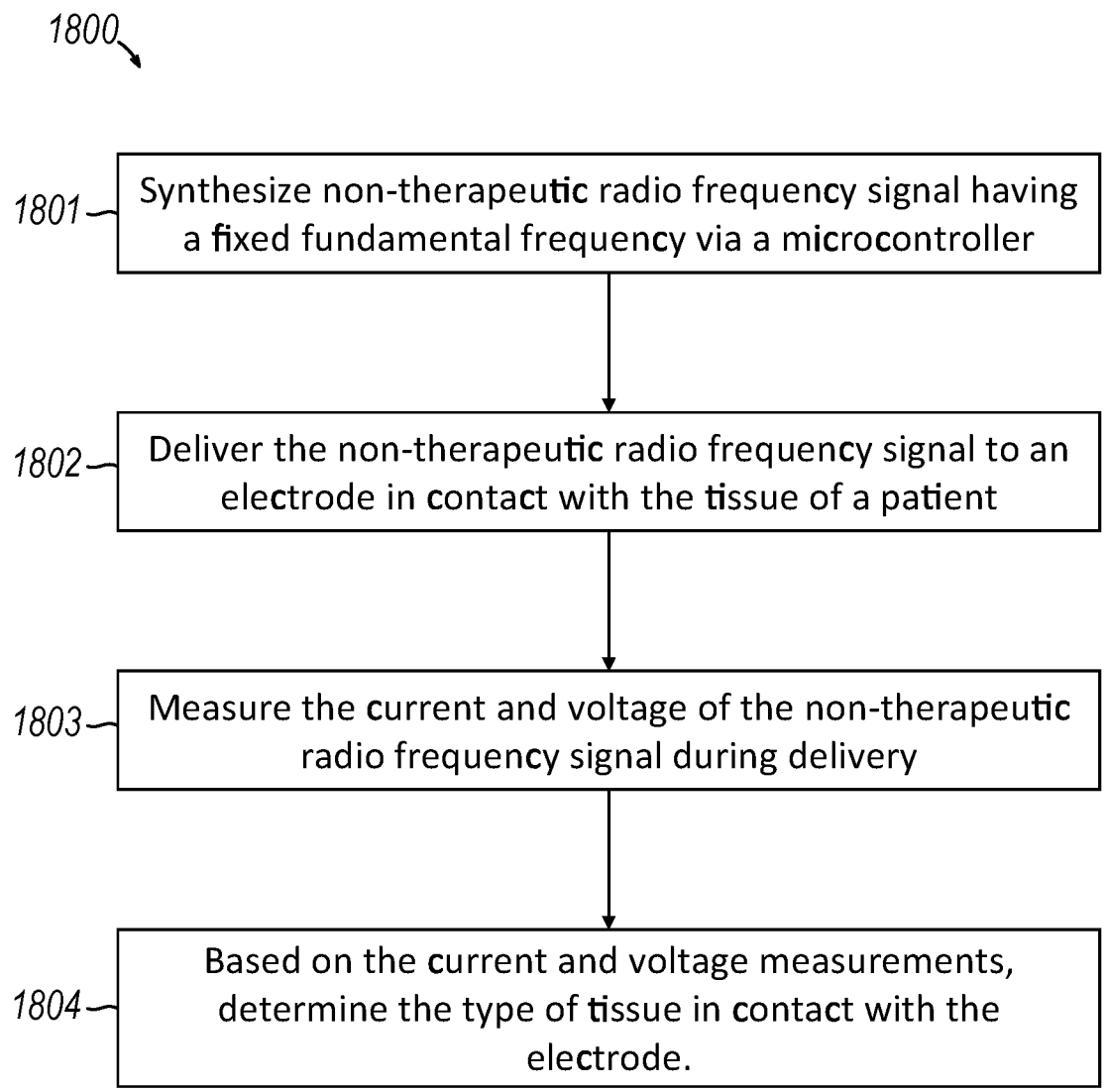
FIG. 18 depicts a flow chart of an illustrative process of utilizing a tissue sensing circuit to determine a presence and a type of tissue placed in contact with electrodes.

FIG. 18 shows an illustrative process (1800) of utilizing tissue sensing circuit (1400) to determine a presence and a type of tissue placed in contact with electrodes (1450). A user may, or software may automatically, activate the tissue sensing circuit (1400) (e.g., microcontroller (1410)) to synthesize a non-therapeutic (e.g., low voltage) signal having a fixed fundamental frequency, at step (1801). Once the waveform is synthesized at step (1801), the surgical instrument (e.g., 10) at step (1802) then facilitates the delivery of an electrical signal, using the microcontroller (1410), to the at least one electrode (1450), where the at least one electrode (1450) is in contact with the tissue of a patient. While the generated waveform is being delivered to the patient tissue via the electrodes (1450), a return signal is measured at step (1803) by the microcontroller (1410), which confirms the presence of tissue at the location of electrodes (1450). At step (1804), the microcontroller (1410) determines at least one characteristic of the detected tissue of the patient, such as a type of the tissue, based on the measurement of the return signal. It will be appreciated that based on the absence of a return signal, the microcontroller (1410) may determine that no tissue is present at the location of electrodes (1450). Based on the determined presence and characteristic of the detected tissue, or based on the determined absence of tissue, the microcontroller (1410) may then direct a responsive action to be taken by the surgical instrument, such as providing a related indication (e.g., visible, audible, and/or tactile) to the operator.

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector configured to interact with in vivo material of a patient, the end effector comprising: (i) a first jaw, (ii) a second jaw configured to cooperate with the first jaw to clamp the in vivo material, and (iii) a first electrode configured to directly contact and deliver an electrical signal to the in vivo material positioned between the first and second jaws; (b) a second electrode configured to receive the electrical signal from the first electrode; and (c) an electrical circuit housed within the end effector, wherein the electrical circuit includes a microcontroller and is configured to: (i) control delivery of the electrical signal to the first electrode such that the electrical signal passes from the first electrode, through the in vivo material, to the second electrode, (ii) determine, based on the electrical signal as received by the second electrode, an electrical impedance associated with the in vivo material, and (iii) determine, based on the electrical impedance, at least one of: (A) a presence of a tissue in the in vivo material, (B) an absence of a tissue in the in vivo material, or (C) a characteristic of a tissue forming at least a part of the in vivo material.

Example 2

The surgical instrument of Example 1, wherein the electrical circuit is further configured to: generate the electrical signal using the microcontroller, wherein the electrical signal comprises a synthesized waveform.

Example 3

The surgical instrument of Example 2, wherein the synthesized waveform has a fixed single fundamental frequency.

Example 4

The surgical instrument of any of Examples 2 through 3, wherein the electrical circuit further includes a band-pass-filter (BPF).

Example 5

The surgical instrument of Example 4, wherein the electrical circuit is configured to pass the synthesized waveform through the BPF prior to delivery to the first electrode.

Example 6

The surgical instrument of any of Examples 1 through 5, wherein the electrical circuit further includes a voltage-controlled-current-source (VCCS) circuit.

Example 7

The surgical instrument of Example 6, wherein the electrical circuit is further configured to: transform, using the VCCS circuit, the electrical signal into a current limited signal.

Example 8

The surgical instrument of any of Examples 1 through 7, wherein the electrical circuit further includes an operational amplifier, wherein the electrical circuit is further configured to: buffer and amplify, using the operational amplifier, the electrical signal prior to the electrical signal returning to the microcontroller from the second electrode.

Example 9

The surgical instrument of any of Examples 1 through 8, wherein the electrical circuit is further configured to: extract and analyze at least one feature from the electrical signal, the at least one feature being a feature selected from the group consisting of an amplitude of the electrical signal and a phase shift of the electrical signal.

Example 10

The surgical instrument of any of Examples 1 through 9, wherein the electrical circuit is further configured to identify a current waveform and a voltage waveform associated with the electrical signal delivered to the in vivo material.

Example 11

The surgical instrument of any of Examples 1 through 10, wherein the electrical circuit is configured to determine the electrical impedance based on a capacitive reactance and an inductive reactance of the in vivo material.

Example 12

The surgical instrument of any of Examples 1 through 11, wherein the first and second electrodes are presented by the end effector.

Example 13

The surgical instrument of any of Examples 1 through 12, wherein the first electrode is presented by the end effector and the second electrode is located remotely from the end effector.

Example 14

The surgical instrument of any of Examples 1 through 13, wherein the end effector further comprises a staple cartridge removably coupled with the second jaw and having a plurality of staples, wherein the microcontroller is secured to a body of the staple cartridge.

Example 15

The surgical instrument of any of Examples 1 through 14, wherein the microcontroller is disposed on an interior surface of one of the first jaw or the second jaw.

Example 16

A surgical instrument, comprising: (a) a body; (b) a shaft extending distally from the body; (c) an end effector at a distal end of the shaft, wherein the end effector includes: (i) a first jaw having a plurality of staple forming pockets configured to form staples, (ii) a second jaw configured to cooperate with the first jaw to clamp in vivo material of a patient, and (iii) a staple cartridge removably coupled with the second jaw and having a plurality of staples; (d) first and second electrodes configured to deliver an electrical signal to the in vivo material positioned between the first and second jaws; and (e) an electrical circuit electrically coupled with the first and second electrodes and including a microcontroller secured to a portion of one of the first jaw, the second jaw, or the staple cartridge, wherein the electrical circuit is configured to: (i) control delivery of the electrical signal to the first electrode such that the electrical signal passes from the first electrode, through the in vivo material, to the second electrode, (ii) determine, based on the electrical signal as received by the second electrode, an electrical impedance associated with the in vivo material, and (iii) determine, based on the electrical impedance, at least one of: (A) a presence of a tissue in the in vivo material, (B) an absence of a tissue in the in vivo material, or (C) a characteristic of a tissue forming at least a part of the in vivo material.

Example 17

The surgical instrument of Example 16, wherein the first and second electrodes are presented by the end effector.

Example 18

The surgical instrument of any of Examples 16 through 17, wherein the electrical circuit further includes at least one of a band-pass-filter (BPF), a voltage-controlled-current-source (VCCS) circuit, or an operational amplifier. wherein the electrical circuit is configured to perform an action selected from the group consisting of: (a) pass a synthesized waveform through the BPF prior to delivery of the electrical signal to the first electrode; (b) transform, using the VCCS circuit, the electrical signal into a current limited signal; and (c) buffer and amplify, using the operational amplifier, the electrical signal prior to the electrical signal returning to the microcontroller from the second electrode.

Example 19

The surgical instrument of any of Examples 16 through 18, wherein the microcontroller is configured to determine the electrical impedance based on a capacitive reactance and an inductive reactance of the in vivo material.

Example 20

A method of operating a surgical instrument having first and second electrodes and an end effector that houses a microcontroller, the method comprising: (a) controlling, using the microcontroller, delivery of an electrical signal to the first electrode, wherein the first electrode is configured to directly contact and deliver the electrical signal to in vivo material clamped by the end effector; (b) receiving the electrical signal with the second electrode after the electrical signal has passed through the in vivo material from the first electrode; (c) determining with the microcontroller, based on the electrical signal as received by the second electrode, an electrical impedance associated with the in vivo material; and (d) determining with the microcontroller, based on the electrical impedance, at least one of: (i) a presence of a tissue in the in vivo material, (ii) an absence of a tissue in the in vivo material, or (iii) a characteristic of a tissue forming at least a part of the in vivo material.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein, in its entirety.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an end effector configured to interact with in vivo material of a patient, the end effector comprising:
      (i) a first jaw,
      (ii) a second jaw configured to cooperate with the first jaw to clamp the in vivo material, and
      (iii) a first electrode configured to directly contact and deliver an electrical signal to the in vivo material positioned between the first and second jaws;
   (b) a second electrode configured to receive the electrical signal from the first electrode; and
   (c) an electrical circuit housed within the end effector, wherein the electrical circuit includes a microcontroller and is configured to:
      (i) control delivery of the electrical signal to the first electrode such that the electrical signal passes from the first electrode, through the in vivo material, to the second electrode,
      (ii) determine, based on the electrical signal as received by the second electrode, an electrical impedance associated with the in vivo material, and
      (iii) determine, based on the electrical impedance, at least one of:
         (A) a presence of a tissue in the in vivo material,
         (B) an absence of a tissue in the in vivo material, or
         (C) a characteristic of a tissue forming at least a part of the in vivo material.

2. The surgical instrument of claim 1, wherein the electrical circuit is further configured to: generate the electrical signal using the microcontroller, wherein the electrical signal comprises a synthesized waveform.

3. The surgical instrument of claim 2, wherein the synthesized waveform has a fixed single fundamental frequency.

4. The surgical instrument of claim 2, wherein the electrical circuit further includes a band-pass-filter (BPF).

5. The surgical instrument of claim 4, wherein the electrical circuit is configured to pass the synthesized waveform through the BPF prior to delivery to the first electrode.

6. The surgical instrument of claim 1, wherein the electrical circuit further includes a voltage-controlled-current-source (VCCS) circuit.

7. The surgical instrument of claim 6, wherein the electrical circuit is further configured to: transform, using the VCCS circuit, the electrical signal into a current limited signal.

8. The surgical instrument of claim 1, wherein the electrical circuit further includes an operational amplifier, wherein the electrical circuit is further configured to: buffer and amplify, using the operational amplifier, the electrical signal prior to the electrical signal returning to the microcontroller from the second electrode.

9. The surgical instrument of claim 1, wherein the electrical circuit is further configured to: extract and analyze at least one feature from the electrical signal, the at least one feature being a feature selected from the group consisting of an amplitude of the electrical signal and a phase shift of the electrical signal.

10. The surgical instrument of claim 1, wherein the electrical circuit is further configured to identify a current waveform and a voltage waveform associated with the electrical signal delivered to the in vivo material.

11. The surgical instrument of claim 1, wherein the electrical circuit is configured to determine the electrical impedance based on a capacitive reactance and an inductive reactance of the in vivo material.

12. The surgical instrument of claim 1, wherein the first and second electrodes are presented by the end effector.

13. The surgical instrument of claim 1, wherein the first electrode is presented by the end effector and the second electrode is located remotely from the end effector.

14. The surgical instrument of claim 1, wherein the end effector further comprises a staple cartridge removably coupled with the second jaw and having a plurality of staples, wherein the microcontroller is secured to a body of the staple cartridge.

15. The surgical instrument of claim 1, wherein the microcontroller is disposed on an interior surface of one of the first jaw or the second jaw.

16. A surgical instrument, comprising:
   (a) a body;
   (b) a shaft extending distally from the body;
   (c) an end effector at a distal end of the shaft, wherein the end effector includes:
      (i) a first jaw having a plurality of staple forming pockets configured to form staples,
      (ii) a second jaw configured to cooperate with the first jaw to clamp in vivo material of a patient, and
      (iii) a staple cartridge removably coupled with the second jaw and having a plurality of staples;
   (d) first and second electrodes configured to deliver an electrical signal to the in vivo material positioned between the first and second jaws; and (e) an electrical circuit electrically coupled with the first and second electrodes and including a microcontroller secured to a portion of one of the first jaw, the second jaw, or the staple cartridge, wherein the electrical circuit is configured to:
  (i) control delivery of the electrical signal to the first electrode such that the electrical signal passes from the first electrode, through the in vivo material, to the second electrode,
  (ii) determine, based on the electrical signal as received by the second electrode, an electrical impedance associated with the in vivo material, and
  (iii) determine, based on the electrical impedance, at least one of:
    (A) a presence of a tissue in the in vivo material,
    (B) an absence of a tissue in the in vivo material, or
    (C) a characteristic of a tissue forming at least a part of the in vivo material.

17. The surgical instrument of claim 16, wherein the first and second electrodes are presented by the end effector.

18. The surgical instrument of claim 16, wherein the electrical circuit further includes at least one of a band-pass-filter (BPF), a voltage-controlled-current-source (VCCS) circuit, or an operational amplifier, wherein the electrical circuit is configured to perform an action selected from the group consisting of:
  (a) pass a synthesized waveform through the BPF prior to delivery of the electrical signal to the first electrode;
  (b) transform, using the VCCS circuit, the electrical signal into a current limited signal; and
  (c) buffer and amplify, using the operational amplifier, the electrical signal prior to the electrical signal returning to the microcontroller from the second electrode.

19. The surgical instrument of claim 16, wherein the microcontroller is configured to determine the electrical impedance based on a capacitive reactance and an inductive reactance of the in vivo material.

20. A method of operating a surgical instrument having first and second electrodes and an end effector that houses a microcontroller, the method comprising:
  (a) controlling, using the microcontroller, delivery of an electrical signal to the first electrode, wherein the first electrode is configured to directly contact and deliver the electrical signal to in vivo material clamped by the end effector;
  (b) receiving the electrical signal with the second electrode after the electrical signal has passed through the in vivo material from the first electrode;
  (c) determining with the microcontroller, based on the electrical signal as received by the second electrode, an electrical impedance associated with the in vivo material; and
  (d) determining with the microcontroller, based on the electrical impedance, at least one of:
    (i) a presence of a tissue in the in vivo material,
    (ii) an absence of a tissue in the in vivo material, or
    (iii) a characteristic of a tissue forming at least a part of the in vivo material.

\* \* \* \* \*